United States Patent
Heigl et al.

(10) Patent No.: US 6,912,471 B2
(45) Date of Patent: Jun. 28, 2005

(54) PROCESSING METHOD FOR A VOLUME DATASET

(75) Inventors: Benno Heigl, Untersiemau (DE); Joachim Hornegger, Baiersdorf (DE); Marcus Prümmer, Criesbach (DE)

(73) Assignee: Siemens Aktiengesellschaft, Munich (DE)

( * ) Notice: Subject to any disclaimer, the term of this patent is extended or adjusted under 35 U.S.C. 154(b) by 41 days.

(21) Appl. No.: 10/626,210

(22) Filed: Jul. 24, 2003

(65) Prior Publication Data

US 2004/0210403 A1 Oct. 21, 2004

(30) Foreign Application Priority Data

Jul. 24, 2002 (DE) ............................. 102 33 668

(51) Int. Cl.⁷ .......................... G06F 19/00; A61B 8/06
(52) U.S. Cl. ................... 702/32; 600/454; 600/465; 600/468
(58) Field of Search ......................... 702/32; 600/419, 600/425, 426, 427, 454, 468, 465; 378/1; 382/128, 130, 131, 132

(56) References Cited

U.S. PATENT DOCUMENTS

| | | | | |
|---|---|---|---|---|
| 6,443,894 B1 | * | 9/2002 | Sumanaweera et al. | 600/443 |
| 6,503,202 B1 | * | 1/2003 | Hossack et al. | 600/454 |
| 6,643,533 B2 | * | 11/2003 | Knoplioch et al. | 600/407 |
| 6,829,379 B1 | * | 12/2004 | Knoplioch et al. | 382/131 |
| 2002/0136440 A1 | * | 9/2002 | Yim et al. | 382/131 |
| 2003/0053697 A1 | * | 3/2003 | Aylward et al. | 382/203 |
| 2004/0249270 A1 | * | 12/2004 | Kondo et al. | 600/425 |
| 2004/0254468 A1 | * | 12/2004 | Herzog et al. | 600/453 |

OTHER PUBLICATIONS

Barnea, "Model–Based Estimation of Coronary Vessel Diameter in Angiographic Images", IEEE, 1998.*
Yfantis et al., "A Digital Viewer With Quantitative Coronary Angiographic Information", IEEE, 1998.*
Guo et al., "Quantitative Evaluation of Multiple Arterial Stenoses using 3D Power Doppler Imaging", IEEE, 1996.*
Dorsaz et al., Three–Dimensional Desitometric Assessment of Coronary Artery Stensosis, IEEE, 1995.*
Wankling et al., "A Computer System for the Quantitification of Coronary Artery Stenoses—Design of the Human Computer Interface", IEEE, 1990.*

* cited by examiner

Primary Examiner—Patrick J. Assouad
(74) Attorney, Agent, or Firm—Schiff Hardin LLP

(57) ABSTRACT

A volume dataset describes at least one tubular vessel and its environment. For processing the volume dataset, an operating point is first defined. A computer then determines slice planes containing the operating point and a sectional area enclosed by the vessel and contained in the respective slice plane for each of the slice planes. Finally, the computer determines the slice plane with the minimum sectional area and determines a working slice plane on the basis of this slice plane.

18 Claims, 6 Drawing Sheets

PROCESSING METHOD FOR A VOLUME DATASET

BACKGROUND OF THE INVENTION

1. Field of the Invention

The present invention is directed to a processing method for a volume dataset that describes at least one tubular vessel and its surroundings.

2. Description of the Prior Art

Processing methods of the above type are particularly utilized for the examination of stenoses in the medical field. Conventionally, a user displays a scan proposal or progression for this purpose, a working slice plane being then shifted along this. The working slice plane thereby proceeds perpendicular to the section of the image under observation at the moment. An arbitrary navigation along the principal axis of the vessel in a vessel structure is highly restricted as a result, and requires a re-selection of the progression along the vessel structure. The inter-activity between automated measurement and manual correction with which the visual evaluation is matched to the physician's requirements is very limited. Such a workflow is unacceptable in the context of a clinical intervention of the subject.

SUMMARY OF THE INVENTION

An object of the present invention is to provide a processing method for a volume dataset with which a considerably more comfortable (user-friendly) navigation through the vessel is possible.

This object is achieved by a processing method wherein an operating point is defined, slice planes containing the operating point are determined by a computer, the computer determines a sectional area enclosed by the vessel and contained in the respective slice plane for each of the slice planes, the computer determines the slice plane with the minimum sectional area, and the computer determines a working slice plane on the basis of the slice plane with the minimum sectional area.

As a result, the working slice plane always proceeds essentially perpendicular to the local principal axis of the vessel independently of the prescribed path.

In an embodiment, the computer determines the center of gravity of the minimum sectional area and a new operating point within the working slice plane is defined on the basis of the center of gravity. This allows the computer to automatically correct the operating point toward the center of gravity. The newly defined operating point preferably lies between the old operating point and the center of gravity. As a result of this only partial correction, the processing method is more stable in terms of noise and minor fluctuations of the vessel contour.

In another embodiment, the user gives the computer tilt commands and the computer tilts the working slice plane around tilting axes in conformity with the prescribed tilt commands. This allows a manual post-correction of the working slice plane determined by the computer. The tilt commands preferably are entered into the computer via a joystick, a mouse or cursor keys of a keyboard. The tilting axes preferably proceed perpendicular to one another.

In another embodiment, the user gives the computer shift commands, and the computer redefines the operating point according to the prescribed shift commands, with a connecting line between the previous operating point and the newly defined operating point proceeding perpendicularly to the working slice plane. The computer redefines the working slice plane according to the steps set forth above, so it is possible to work through the vessel in a simple way by shifting the working slice plane. Analogous to the tilt commands, the shift commands can be entered via cursor keys of a keyboard, a mouse or a joystick.

In a further embodiment, the computer determines a perspective projection of the volume dataset proceeding from a projection center into an image plane and displays it on a viewing device. This allows a user to comprehend the connotational content of the volume dataset especially simply and intuitively.

The volume dataset can be evaluated even more easily when the computer co-displays the working slice plane in the perspective projection.

The evaluation of the volume dataset is even easier when the computer also co-displays a section through the volume dataset on the viewing device that is determined by the working slice plane.

The determination of the operating point is especially easy and user-friendly for a user in an embodiment wherein a user prescribes a picture element of the image plane for the computer, the computer determines the projection ray on the basis of the projection center and the picture element, the computer determines an intersection of the projection ray with the vessel, and the computer determines the operating point on the basis of the intersection.

The prescription of the picture element is especially simple when it is prescribed for the computer by positioning a cursor and input of an acknowledge command.

As an alternative to a user prescribing the operating point, it is also possible for the computer to determine the slice plane with minimum sectional area for a number of possible operating points according to the steps initially described, and for the computer to determine a characteristic value for each of these minimum planes of section, and for the computer to define one of the possible operating points as the operating point on the basis of an evaluation criterion for the characteristic values. For example, the characteristic value can be the area dimension itself, a minimum expanse or a maximum expanse of the minimum planes of section.

That operating point among the possible operating points at which the characteristic value of the corresponding minimum sectional area is minimal is preferably selected as the "determined" operating point, The processing method is further improved in an embodiment wherein the computer co-displays the identified characteristic values on the viewing device as a function of the provisional operating point.

The determination of the operating point can more rapidly accomplished be accomplished in an embodiment. Wherein a user prescribes a starting point and an ending point for the computer such that the minimum sectional area of a slice plane, determined with respect to the starting point and having the vessel with the minimum sectional area, is arranged at a different location than the minimum sectional area of a slice plane determined with respect to the ending point and having the vessel with minimum sectional area. The possible operating points with respect to the vessel lie between the starting point and the ending point.

DESCRIPTION OF THE PREFERRED EMBODIMENTS

Figure 1:
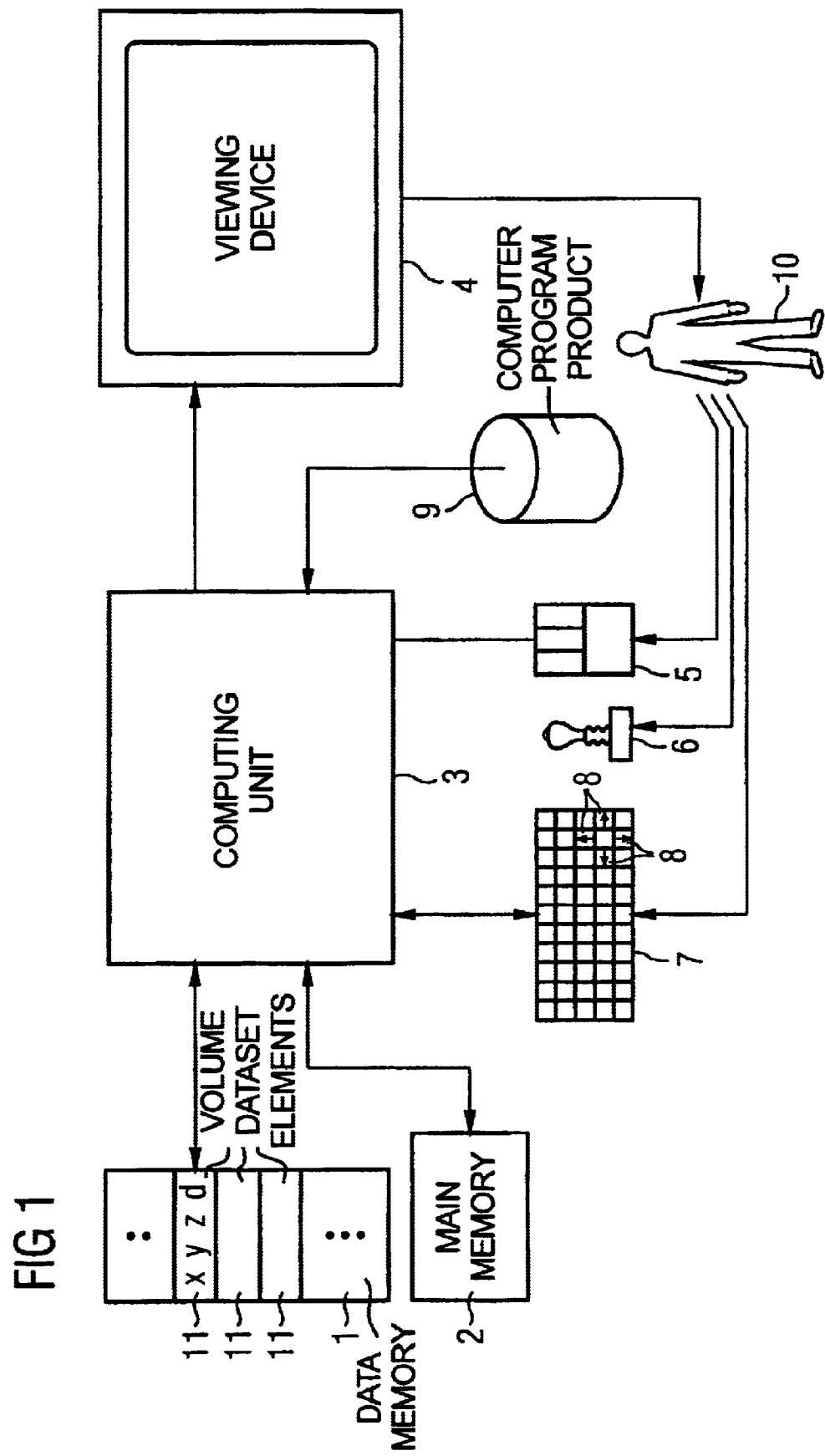
FIG. 1 illustrates the basic components of a computer for executing the inventive method.

As shown in FIG. 1, a computer has a data memory 1 and a main memory 2 that are connected to a computing unit 3. A viewing device 4, for example a monitor 4, as well as input units 5 through 7 are connected to the computing unit 3. The input units 5 through 7 include, for example, a mouse 5, a joystick 6 and a keyboard 7. In particular, the keyboard 7 has cursor keys 8.

The computing unit 3 processes a computer program product 9 with which the computer is programmed. In the course of processing the computer program product 9, the computing unit 3 accesses—among other things—the data memory 1 and the main memory 2, receives inputs from the input units 5 through 7 and delivers outputs via the viewing device 4. The inputs ensue from a user 10; the outputs ensue to the user 10.

Figure 2:
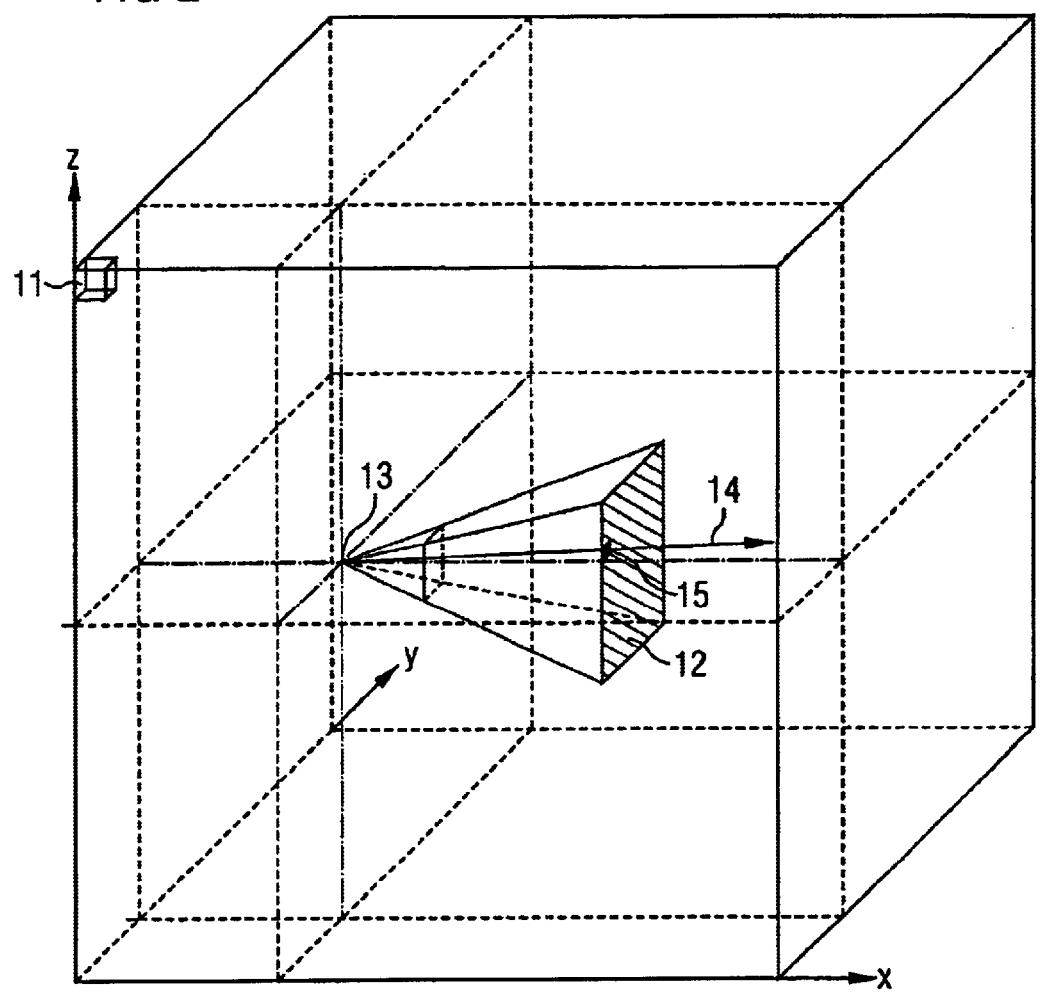
FIG. 2 is a perspective view of a volume dataset to be processed in accordance with the inventive method.

A volume dataset is stored in the data memory 1. The volume dataset is composed of a number of volume dataset elements 11. Three coordinates x, y, z of a coordinate systems and a data value d are allocated to each volume dataset element 11. Typically, the coordinate system is a right-hand, rectangular Cartesian coordinate system. One of the volume dataset elements 11 is shown in FIG. 2 as an example.

The computer is able to determine a two-dimensional perspective projection into an image plane 2 and present it on the viewing device 4. This is schematically indicated in FIG. 2. The perspective projection proceeds from a projection center 13. The computer calculates the appertaining image data values for a number of picture elements 15 on the basis of projection rays 14 emanating from the projection center 13. The perspective projection determined in this way is then presented on the viewing device 4.

Figure 3:
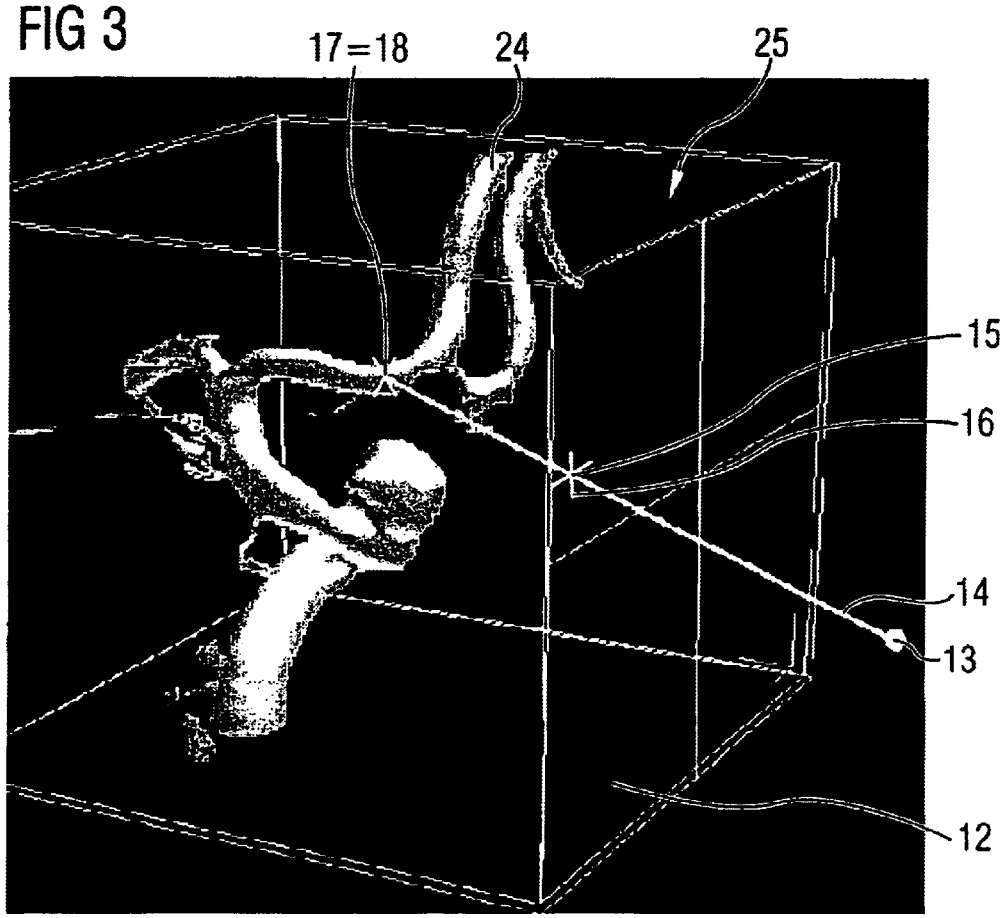
FIG. 3 is a further perspective view of the volume dataset.

As shown in FIG. 3, the volume dataset describes a vascular system with tubular vessels 24 and their environment 25. Methods for locating the vessels 24 in the environment 25 on the basis of the data values d of the volume dataset elements 11 are well known. Methods with which the vascular system itself can be emphasized from the environment 25, or with which the environment 25 can be blanked out, are likewise known.

The user 10 prescribes a picture element 15 of the image plane 12 for the computer. This occurs in that, for example, by the user 10 positioning a cursor 16 and then entering a confirmation command. For example, the cursor 16 can be positioned with the cursor keys 9, and an enter key of the keyboard 7 is then pressed. Alternatively, the cursor 16, for example, can be positioned with the mouse 5, and the position is confirmed by actuation of a mouse key. Positioning and confirmation with the joystick 6 is also possible in a similar way.

The projection center 13 and the selected picture element 15 define a projection ray 14. On the basis of the projection center 13 and the picture element 15, the computer therefore determines this projection ray 14 and tracks it into the volume until it encounters a vessel 24. When the projection ray 14 encounters a vessel 24, this corresponds to an intersection 17 of the projection ray 14 with the vessel 24. The computer then determines an operating point 18 on the basis of this intersection 17. The operating point 18 can be identical to the intersection 17, Proceeding from the operating point 18, the computer then defines a number of directions within a hemisphere. Some of these directions are shown as an example in FIG. 4. The computer then defines the slice planes through the operating point 18 that are perpendicular to the directions. The computer then calculates a sectional area for each of these slice planes. The sectional area is defined as being contained in the respective slice plane and enclosed by the vessel 24. The computer then determines a working slice plane 19 by comparing the planes of section to one another. The working slice plane 19 is a slice plane among the multiple slice planes, that has the minimum sectional area.

It has proven adequately precise in practice to fix the individual directions with respect to which the slice planes are determined in the following way. One direction proceeds parallel to the z-axis. Four directions describe an angle of 22.5° with the z-axis and are uniformly distributed on an annulus defined in this way. Eight directions describe an angle of 45° with the z-axis and are likewise uniformly distributed on an annulus defined in this way. The same is true of twelve directions that describe an angle of 67.5° with the z-axis. Sixteen direction vectors that proceed perpendicular to the z-axis are likewise respectively offset by 22.5° relative to one another in the xy-plane.

Generally, the working slice plane 19 is determined with adequate precision by means of these direction vectors. As warranted, however, a more precise optimization can ensue in a second execution.

Usually, the operating point determined on the basis of the designation of the picture element 15 lying at the edge of the vessel 24. In order to center this operating point 18 better, the computer determines the center of gravity 20 of the minimum sectional area. The computer then determines a new operating point 18' within the working slice plane 19 on the basis of the center of gravity 20. For stability reasons, the newly defined operating point 18' preferably lies between the old operating point 18 and the center of gravity 20.

Figure 5:
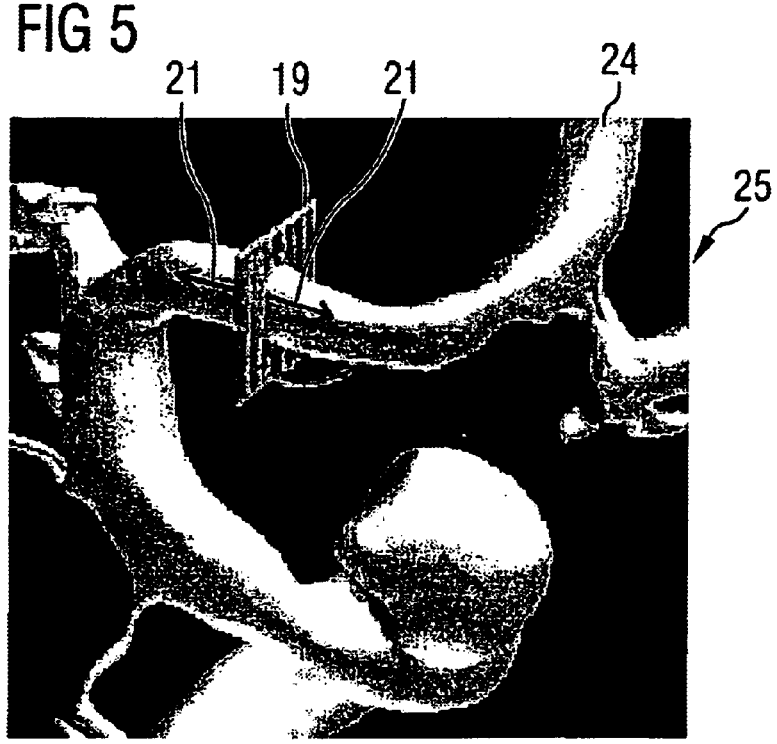
FIG. 5 combines the illustration of FIG. 3 together with a working slice plane.

As proceeds from the illustration according to FIG. 5, the computer co-displays the working slice plane 19 in the perspective projection. Two directional arrows 21 are also entered in FIG. 5. These directional arrows 21 proceed perpendicularly to the working slice plane 19. The working slice plane 19 can be shifted in the directions indicated by the directional arrows 21. This occurs in the way set forth below.

The user 10 gives the computer a shift command. The prescription of the shift command optionally ensues with the cursor keys 8, the mouse 5 or (preferably) via the joystick 6. Entry of an acknowledge command is possible but not compulsory.

As a result of the shift command, the computer determines a new operating point 18 dependent on the shift direction. A connecting line between the previous operating point 18 or 18' and the newly defined operating point 18 thereby proceeds along the directional arrow 21, i.e. perpendicular to the working slice plane 19. The working slice plane 19 is defined anew for the now newly defined operating point 18 according to the method explained in conjunction with FIG.

4. As warranted, the operating point 18 is again shifted toward the center of gravity 20 of the newly identified, minimum sectional area. As a result, the operating point gradually approaches the principal vessel axis.

Figure 6:
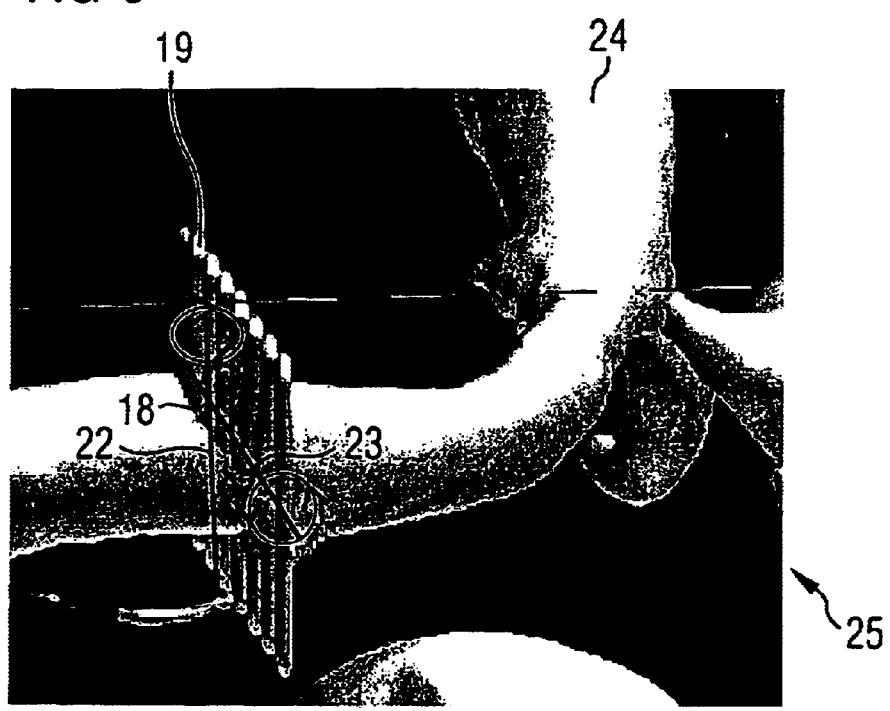
FIG. 6 is an excerpt from FIG. 5.

As can be seen particularly clearly from FIG. 6, the working slice plane 19 can be tilted around tilting axes 22, 23. The tilting axes 22, 23 intersect at a right angle in the operating point 18. The tilting axes 22, 23 shown in FIG. 6 preferably are mixed in only when the user 20 indicates a tilt request to the computer. The indication of a tilt request can ensue, for example, by the user 10 entering a specific preliminary command. When, for example, the user 10 actuates a specific key of the mouse 5, the joystick 6 or the keyboard 7, then the computer interprets this as indicating that a following actuation of the cursor keys 8, of the mouse 5 or of the joystick 6 is not to be utilized for a displacement of the working slice plane 19, but for a tilting thereof. The user 10 therefore also gives the tilt commands themselves to the computer via the joystick 6, the mouse 5 or the cursor keys 8 of the keyboard 7. In conformity with the prescribed tilt commands, the computer then tilts the working slice plane 19 around the tilting axes 22, 23. A shift of the operating point 18, however, does not occur after a tilting of the working slice plane 19.

Figure 7:
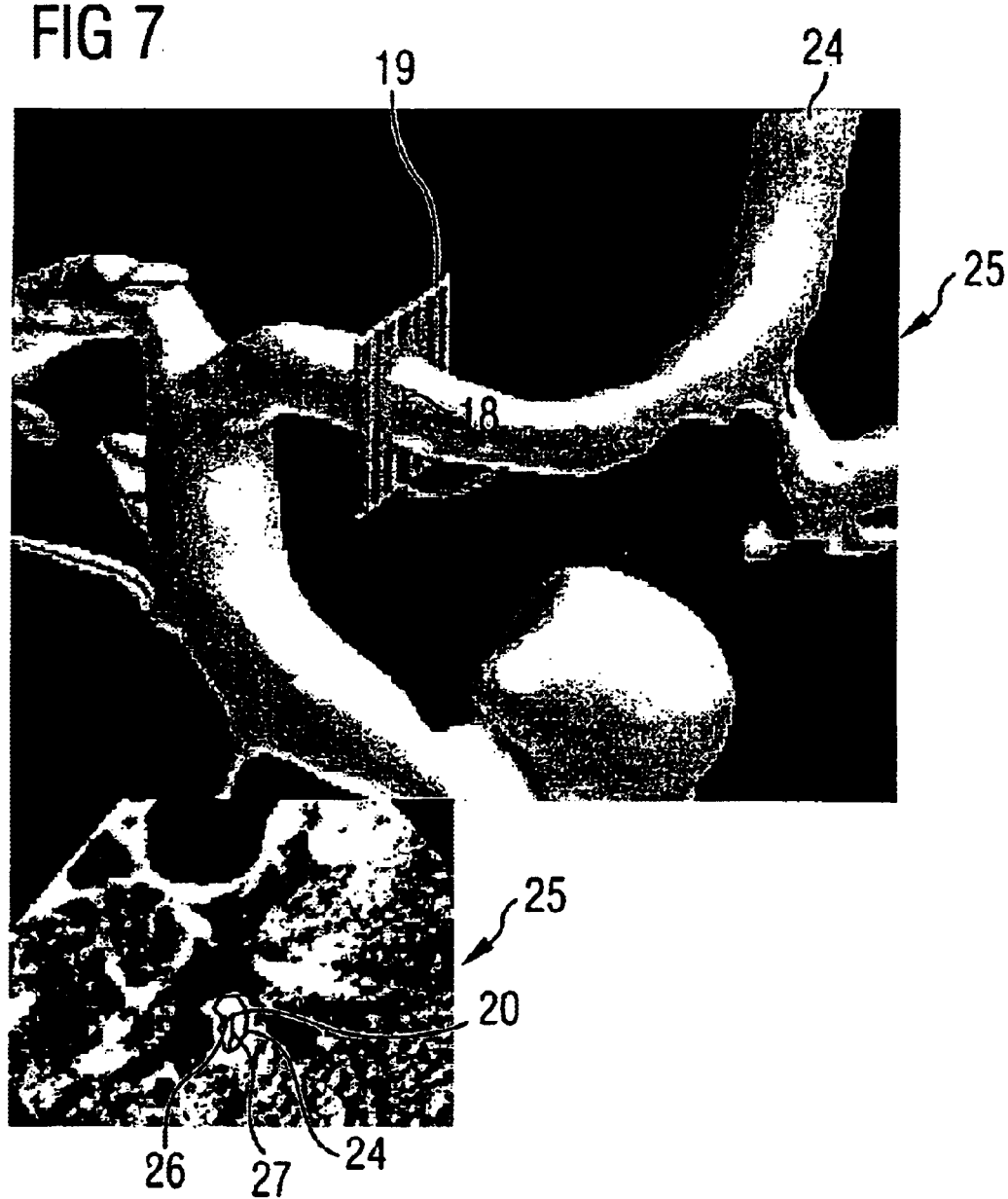
FIG. 7 is a supplementary illustration relating to FIG. 5.

As can be seen from FIG. 7, the computer also can co-display a section through the volume dataset defined by the working slice plane 19 on the display device 4 together with the perspective projection. This presentation preferably shows not only the vessel 24 itself but also its environment 25. Further, a minimum radius 26 and a maximum radius 27 for the vessel 24 preferably are also entered in these presentations. The radii 26, 27 proceed from the center of gravity 20.

In the above-described processing method, the computer determines the operating point 18 on the basis of an unambiguous prescription by the user 10. Although the operating point 18 might be corrected again within the working slice plane 19 that has been found, it is not independently determined by the computer. However, it is also possible for the computer to determine the operating point 18 exclusively on the basis of the vessel 24 itself. This is explained in detail below in conjunction with FIG. 8.

Figure 8:
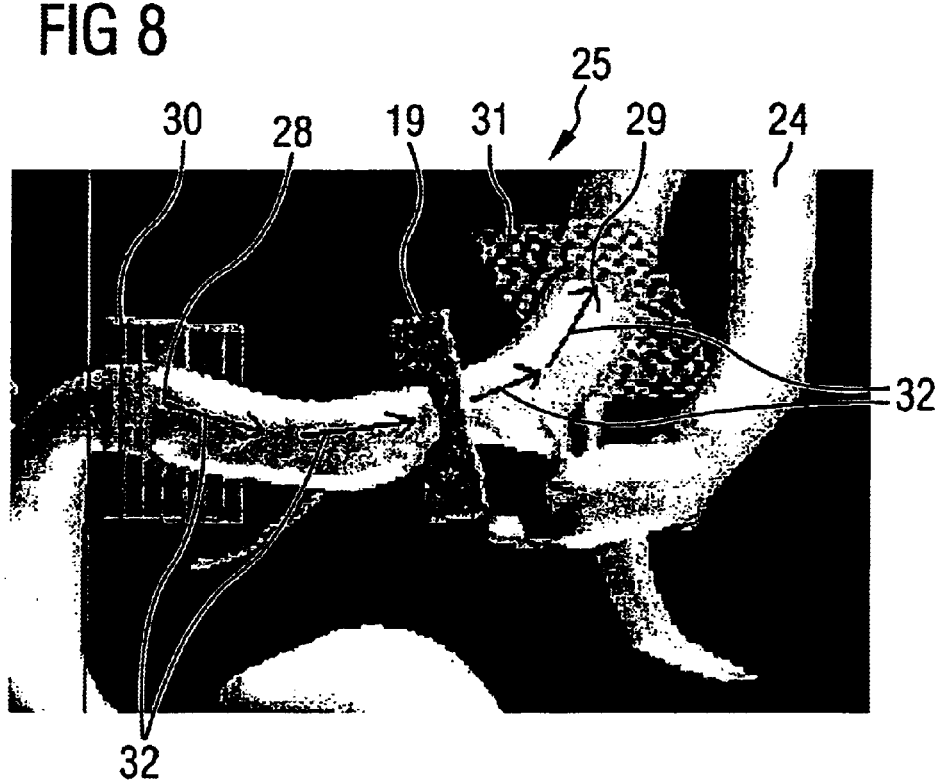
FIG. 8 is another perspective view of a volume dataset.

As shown in FIG. 8, the user 10 first prescribes a starting point 28 and an ending point 29 for the computer. The computer then determines a starting slice plane 30 and an ending slice plane 31 with respect to these two points 28, 29. Within the starting slice plane 30, further, it corrects the starting point 28 in the direction of the center of gravity of the sectional area of the identified starting slice plane 30 with the vessel 24. It likewise corrects the ending point 29 in the direction toward the center of gravity of the sectional area of the ending slice plane 31 with the vessel 24. The prescription of the starting point 28, the determination of the starting slice plane 30 as well as the correction of the starting point 28 within the starting slice plane 30 ensue entirely analogous to the prescription of the operating point 18, the determination of the working slice plane 19 and the correction of the operating point 18 according to FIG. 4. With respect to the starting point 28, the starting slice plane 30 thus contains the minimum sectional area with the vessel 24. The same is true of the ending slice plane 31 and the ending point 29. It is clear according to FIG. 8 that the minimum planes of section of these planes 30, 31 are arranged at locations that differ from one another. A region of the vascular system is thus pre-selected by the prescription of the starting point 28 and the ending point 29. The computer then independently determines the operating point 18 within this region.

Figure 4:
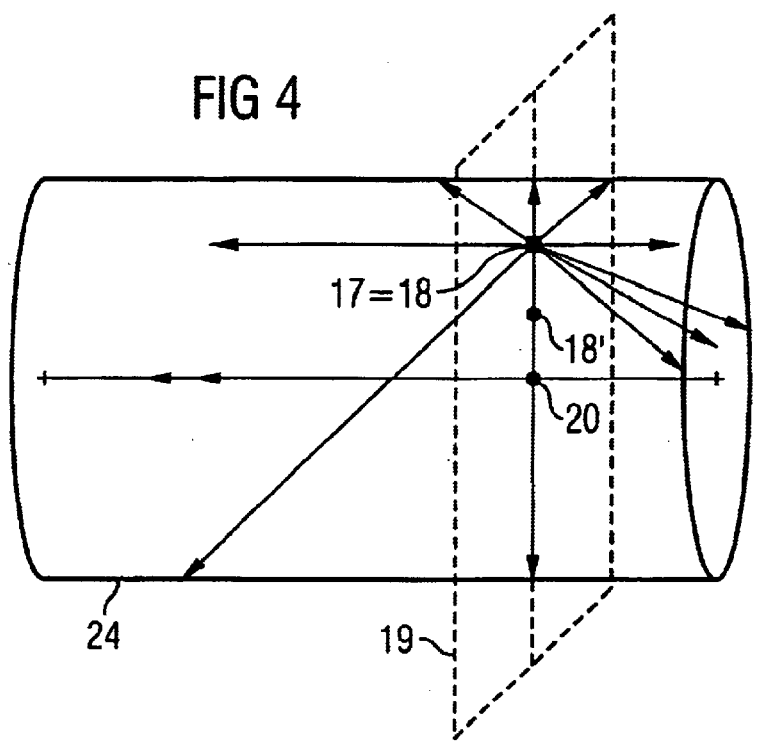
FIG. 4 illustrates the determination of a working slice plane, in accordance with the inventive method.

As schematically indicated in FIG. 8 by arrows 32, the computer successively determines a number of possible operating points within this region and determines the corresponding, possible working slice plane for each of these candidate operating points according to the method described in conjunction with FIG. 4. With respect to the vessel 24, thus, the possible operating points lie between the starting point 28 and the ending point 29.

The respective slice plane with the minimum sectional area is also determined. The computer determines a characteristic value for each of these minimum planes of section. For example, the characteristic value can be the size of the sectional area itself. Alternatively, it can correspond to one of the radii 26, 27 for the respective sectional area. The computer then defines one of the possible operating points as operating point 18 on the basis of an evaluation criterion.

The processing method preferably is employed in the medical field for locating and diagnosing stenoses, i.e. vascular constrictions. The operating point from the candidate operating points is therefore preferably defined as the operating point 18 at which the characteristic value of the corresponding minimum slice plane itself is in turn minimum.

Figure 9:
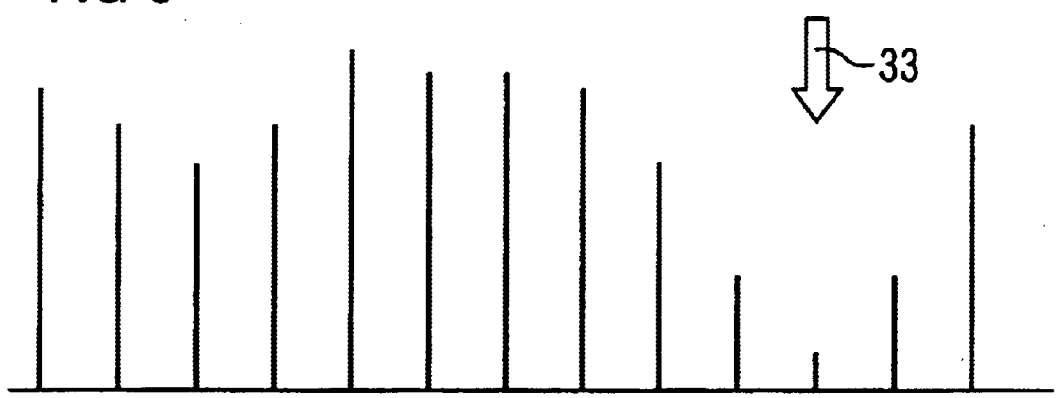
FIG. 9 shows a functional curve of a characteristic value for use in the inventive method.

As schematically shown in FIG. 9, the computer can co-display the identified characteristic values on the viewing device 4 as a function of the provisional operating point. The actual operating point 18 is preferably is emphasized by a marking 33.

An automatic determination of the local vessel orientation (vessel axis) thus can be made in a simple way by means of the above-described processing method, despite the prescription of only a single point, namely the intersection 17 of a projection ray 14 with the vessel 24. As a result, the user interface to the user 10 can be substantially simplified. In particular, a stenosis can be determined and displayed in a simple way in semi-automatic fashion (interactively) or even fully automatically. Forward and a reverse navigation also are considerably simplified. Even a correction of the working slice plane 19 is possible in a simple way by tilting around the tilting axes 22, 23. In particular, the acceptance of such a computer-supported processing method can be considerably increased in the clinical field.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for processing a volume dataset that represents at least one tubular vessel and an environment of the vessel, said method comprising the steps of:
    (a) defining an operating point in said volume dataset;
    (b) in a computer, electronically determining multiple slice planes in said volume dataset containing said operating point;
    (c) in said computer, electronically determining, for each of said slice planes, a sectional area enclosed by the vessel in the respective slice plane;
    (d) in said computer, electronically determining the slice plane, among said multiple slice planes, wherein the sectional area is a minimum; and
    (e) in said computer, electronically determining a working slice plane based on the slice plane containing the minimum sectional area.

2. A method as claimed in claim 1 comprising in said computer, electronically determining a center of gravity of the minimum sectional area and defining a new operating point in said working slice plane based on said center of gravity.

3. A method as claimed in claim 2 comprising defining said new operating point as a new operating point between the initially defined operating point and the center of gravity.

4. A method as claimed in claim 1 comprising the additional steps of:

manually entering tilt commands into said computer; and in said computer, tilting said working slice plane around respective axes according to said tilt commands.

5. A method as claimed in claim 4 comprising entering said tilt commands into said computer via an input unit selected from the group consisting of a joy stick, a computer mouse, and cursor keys of a computer keyboard.

6. A method as claimed in claim 1 comprising the additional steps of:

manually entering shift commands into said computer;

in said computer, electronically redefining said operating point according to said shift commands, with a connecting line between the operating point defined in step (a) and a redefined operating point proceeding perpendicularly to said working slice plane; and in said computer, electronically redetermining said working slice plane by repeating steps (a) through (e) with said redetermined operating point as the operating point in step (a).

7. A method as claimed in claim 6 comprising entering said shift commands into said computer via an input unit selected from the group consisting of a joy stick, a computer mouse, and cursor keys of a computer keyboard.

8. A method as claimed in claim 1 comprising in said computer, determining a perspective projection of said volume dataset proceeding from a projection center into an image plane, and displaying said perspective projection on a viewing device.

9. A method as claimed in claim 8 comprising displaying said working slice plane in said perspective projection on said viewing device.

10. A method as claimed in claim 8 comprising displaying a section through said volume dataset defined by said working slice plane on said viewing device.

11. A method as claimed in claim 8 comprising:

via said computer, manually prescribing a picture element of said image plane;

in said computer, electronically determining a projection ray based on said projection center and said picture element;

in said computer, electronically determining an intersection of said projection ray with the vessel; and in said computer, electronically determining said operating point based on said intersection.

12. A method as claimed in claim 11 wherein the step of prescribing said picture element comprises selectively positioning a cursor on said viewing device and entering an enter command via said computer.

13. A method as claimed in claim 1 wherein step (a) comprises defining a plurality of candidate operating points and wherein said computer executes steps (b), (c), (d) and (e) for each of said candidate operating points, thereby obtaining a plurality of minimum sectional areas, and comprising the additional steps of:

in said computer, electronically determining a characteristic value for each of said minimum sectional areas; and selecting one of said candidate operating points as the operating point for determining said working slice plane in step (e) by evaluating the respective characteristic values of the plurality of minimum sectional areas according to a predetermined evaluation criterion.

14. A method as claimed in claim 13 comprising employing a value associated with each sectional area, as said characteristic value, selected from the group consisting of area, dimension, minimum expanse and maximum expanse.

15. A method as claimed in claim 13 wherein the step of selecting said operating point from among said candidate operating points comprises selecting an operating point an the operating point for use in step (e) for which the characteristic value of the corresponding minimum sectional area is a minimum.

16. A method as claimed in claim 13 comprising, for each of the candidate operating points, displaying said characteristic value as a function of the respective candidate operating point on a viewing device.

17. A method as claimed in claim 13 comprising:

via said computer, manually prescribing a starting point and an ending point;

in said computer, electronically determining a slice plane having a minimum sectional area enclosed by the vessel with regard to said starting point, and electronically determining a different slice plane having a minimum sectional area enclosed by the vessel with regard to the ending point; and selecting said candidate operating points as points with respect to the vessel disposed between said starting point and said ending point.

18. A computer program product loadable into a computer for processing a volume dataset that represents at least one tubular vessel and an environment of the vessel, by causing said computer to, for a defined operating point in said volume dataset:

determine multiple slice planes in said volume dataset containing said operating point;

determine, for each of said slice planes, a sectional area enclosed by the vessel in the respective slice plane;

determine the slice plane, among said multiple slice planes, wherein the sectional area is a minimum; and determine a working slice plane based on the slice plane containing the minimum sectional area.

\* \* \* \* \*